United States Patent [19]
Palermo et al.

[11] Patent Number: 5,986,097
[45] Date of Patent: Nov. 16, 1999

[54] SPIRO[CYCLOPENT[B]INDOLE-PIPERIDINES]

[75] Inventors: Mark G. Palermo, Netcong, N.J.; Gerard J. O'Malley, Newton, Pa.

[73] Assignee: Hoechst Marion Roussel, Inc., Bridgewater, N.J.

[21] Appl. No.: 09/035,276

[22] Filed: Mar. 9, 1998

Related U.S. Application Data

[62] Division of application No. 08/801,290, Feb. 18, 1997, Pat. No. 5,576,743
[60] Provisional application No. 60/046,851, Apr. 10, 1996, abandoned.

[51] Int. Cl.$^6$ .................................................. C07D 221/20
[52] U.S. Cl. ...................................................... 546/16
[58] Field of Search .................................................. 546/16

[56] References Cited

U.S. PATENT DOCUMENTS 5,350,762  9/1994  Martin et al. .

FOREIGN PATENT DOCUMENTS

| 0 412 820 | 2/1991 | European Pat. Off. . |
| 0 413 516 | 2/1991 | European Pat. Off. . |
| 0 670 313 | 9/1995 | European Pat. Off. . |
| WO 94/17045 | 8/1994 | WIPO . |

OTHER PUBLICATIONS

Chem. Abstr., Cliffe et al., vol. 114 1991, ref.: 114:23397W.
Crooks, P.A. et al., J. Chem. Soc. Perkin Trans. 1, 1979, Cambridge, pp. 2719–2726.
Sen. S. et al., Acta Pharm. Jugosl., vol. 39, 1989, pp. 193–200.
Soni, N. et al., Indian J. Pharm. Sci., vol. 45, No. 2 (Mar. 1983) pp. 74–76.
Breiman, R. et al., Isr. J. Chem., vol. 9 (1971) pp. 57–61.
Kalgutkar, A.S. et al., Med. Res. Rev., vol. 15.,No. 4 (1995) pp. 325–388.
Yu, P.H. et al., Gen. Pharmacol., vol. 25, No. 8 (1994) Oxford, pp. 1527–1539.
Cliffe, I.A. et al., J. Med. Chem., vol. 35, No. 7 (Apr. 3, 1992) pp. 1169–1175.
Jucker, E. et al, Helv. Chim. Acta., vol. 49, No. 3 (1966) pp. 1135–1145.
Carrera, G.M. et al., J. Heterocyclic. Chem., vol. 29 (1992) pp. 847–852.
Yoneda, R. et al., J. Org. Chem, vol. 56 (1991) pp. 1827–1832.

*Primary Examiner*—Patricia L. Morris
*Attorney, Agent, or Firm*—Frommer Lawrence & Haug LLP

[57] ABSTRACT

Novel spiro[cyclopent[b]indole-piperidines], intermediates and processes for the preparation thereof, and methods of relieving memory dysfunction and treating depression utilizing the spiro[cyclopent[b]indole-piperidines] and intermediates, or compositions thereof are disclosed.

5 Claims, No Drawings

SPIRO[CYCLOPENT[B]INDOLE-PIPERIDINES]

This application is a divisional of application Ser. No. 08/801,290 filed Feb. 18, 1997, now U.S. Pat. No. 5,576,743 granted May 26, 1998, which application claims the benefit of Provisional application Ser. No. 60/046,851 filed Apr. 10, 1996, now abandoned.

The present invention relates to spiro[cyclopentblindole-piperidines]. More particularly, the present invention relates to spiro[cyclopentblindole-piperidines] of formula 1

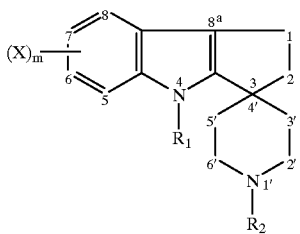

wherein X is hydrogen, halogen, loweralkoxy, loweralkyl, hydroxy, trifluoromethyl and m is 1 or 2 or a group of the formula

wherein R is loweralkyl and $R_3$ is hydrogen or loweralkyl; $R_1$ is hydrogen or loweralkyl; $R_2$ is hydrogen, a group of the formula

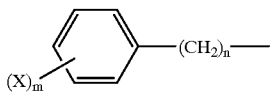

wherein n is 1 or 2 and X and m are as above, a group of the formula

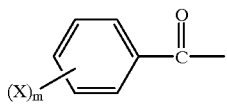

wherein X and m are as above, or a group of the formula

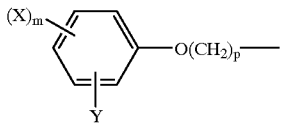

wherein X and m are as above, Y is hydrogen, or a group of the formula

wherein $R_4$ is hydrogen or loweralkyl and p is 2 or 3; the optical isomers thereof; or the pharmaceutically acceptable acid addition salts thereof useful in relieving memory dysfunction and thus indicated in the treatment of Alzheimer's disease, as well as useful in the treatment of depression.

Subgeneric to the compounds of formula 1 are those wherein $R_2$ is hydrogen or a group of the formula

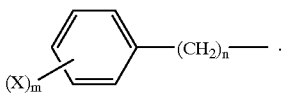

The present invention relates to (N'-phenyl)hydrazones of formula 2

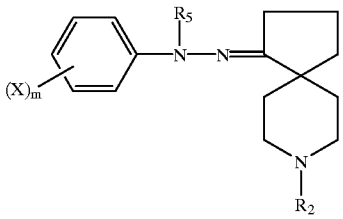

wherein $R_2$ is hydrogen or loweralkyl; $R_5$ is hydrogen or loweralkyl; and X is hydrogen, halogen, loweralkoxy, loweralkyl, hydroxy or trifluoromethyl and m is 1 or 2; the optical isomers thereof; or the pharmaceutically acceptable salts thereof, useful as intermediates for the preparation of the spiro[cyclopent[b]indole-piperidines] of formula 1 and also for the treatment of depression, and 4-cyanopiperidines of formula 3

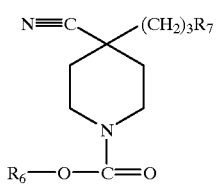

wherein $R_6$ is loweralkyl; and $R_7$ is halogen or cyano, useful as intermediates for the preparation of the spiro[cyclopent[b]indole-piperidines] of formula 1.

As used throughout the specification and appended claims, the term "alkyl" refers to a straight or branched chain hydrocarbon radical containing no saturation and having 1 to 8 carbon atoms. Examples of alkyl groups are methyl, ethyl, 1-propyl, 2-propyl, 1-butyl, 1-hexyl, 3-hexyl, 4-heptyl, 2-octyl and the like. The term "alkoxy" refers to a monovalent substituent which consists of an alkyl group linked through an ether oxygen having its free valence bond from the ether oxygen. Examples of alkoxy groups are methoxy, ethoxy, propoxy, 1-butoxy, 1-pentoxy, 3-hexoxy, 4-heptoxy, 2-octoxy and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol and the like. The term "halogen" refers to a member of the family fluorine, chlorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel spiro[cyclopen[b]indole-piperidines] of the present invention are prepared by the processes delineated in Reaction Scheme A.

To prepare a spiro[cyclopent[b]indole-piperidine] of formula 1 an 8-azaspiro[4.5]decane-1-one 4 is condensed with a phenylhydrazine of formula 5

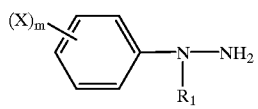

wherein $R_1$ is hydrogen or loweralkyl and X and m are as above to provide a phenylhydrazone of formula 2 wherein $R_1$, X and m are as above, which is cyclized to a spiro [cyclopent[b]indole-piperidine] 1 wherein $R_1$, X and m are as above and $R_2$ is hydrogen. The condensation is carried out by treating the cyclopentanone 4 with a phenylhydrazine 5 in the presence of an organic carboxylic acid such as acetic acid or a mineral acid such as hydrochloric acid in an alkanol such as ethanol at an elevated temperature such as that within the steam bath range to provide 2.

The cyclization is accomplished by treating a phenylhydrazone 2 with an aqueous alkanolic mineral acid such as ethanolic hydrogen chloride at a temperature within the steam bath range to provide 1.

To fabricate a 1'-benzoylspiro[cyclopent[b]indole-piperidine] 1 wherein $R_1$ is loweralkyl, $R_2$ is

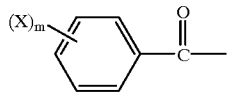

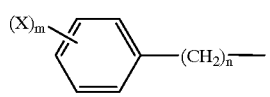

and X, m and n are as above or a 1'-phenylethylspiro [cyclopent[b]indole-piperidine] 1 wherein $R_1$ is loweralkyl and $R_2$ is wherein X, m and n are as above, a spiro[cyclopent [b]indole-piperidine] 1 wherein $R_1$ is loweralkyl, $R_2$ is hydrogen and X and m are as above is treated with a benzoyl halide of formula 6

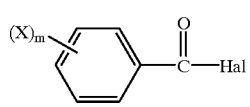

wherein X and m are as above and Hal is bromo or chloro or a phenylalkyl halide of formula 7

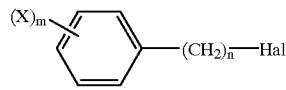

wherein X, m, n and Hal are as above in the presence of a triloweralkylamine such as triethylamine in a halocarbon solvent such as dichloromethane at a temperature within the range from about 0° C. to about ambient temperature, or an alkali metal carbonate such as potassium carbonate in an organic solvent such as acetonitrile at a temperature of about the reflux temperature of the reaction medium.

Similarly, a 1'-phenoxyalkylspiro[cyclopent[b]indole-piperidine] 1 wherein $R_1$ is loweralkyl and $R_2$ is a group of the formula

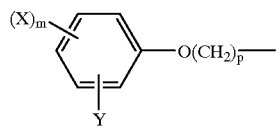

wherein X and m are as above, Y is hydrogen or a group of the formula

wherein $R_4$ is hydrogen or loweralkyl and p is 2 or 3 is prepared by treating a spiro[cyclopent[b]indole-piperidine] 1 wherein $R_1$ is hydrogen or loweralkyl, $R_2$ is hydrogen and X and m are as above with a phenoxyalkylhalide of formula 8

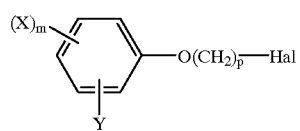

wherein X, Y, m, p and Hal are as above and an inorganic base such as cesium carbonate in an organic solvent such as acetonitrile at a temperature of about 80° C.

The preparation of the starting material, 8-azaspiro[4,5] decane-1-one 4, for the elaboration of the spiro[cyclopent [b]indole-piperidines] of the present invention is outlined in Reaction Scheme B and exemplified in the Examples. In this process, commercially available 4-acetamidopiperidine 9 is acylated to N-ethoxycarbonyl-4-acetamidopiperidine 10, which in turn is converted to 4-cyano-N-ethoxycarbonylpiperdine 11 and then alkylated to 4-(3-chloropropyl)4-cyano-N-ethoxycarbonylpiperidine 12. 4-(3-Chloropropyl)-4-cyano-N-ethoxycarbonylpiperidine 12 is converted to 4-cyano4-(3-cyanopropyl)-N-ethoxycarbonyl piperidine 13, which is cyclized to 4-cyano-1-imino-8-azaspiro[4,5]decane 14 and hydrolyzed to 1. While the process for the synthesis of the starting material 4 for the preparation of the ultimate spiro[cyclopent[b] indole-piperidines] 1 is illustrated with N-ethoxycarbonylpiperidines (10 to 14), the scheme is equally applicable for N-loweralkoxycarbonylpiperidines.

REACTION SCHEME A

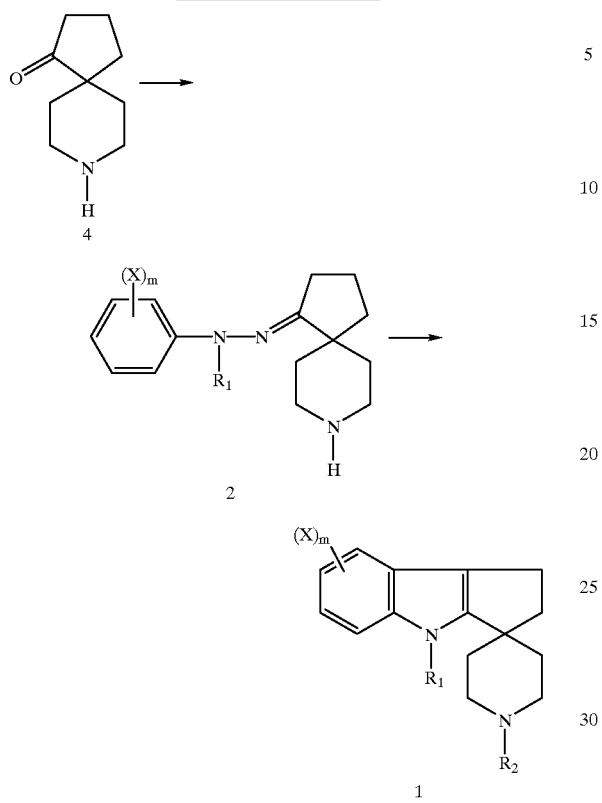

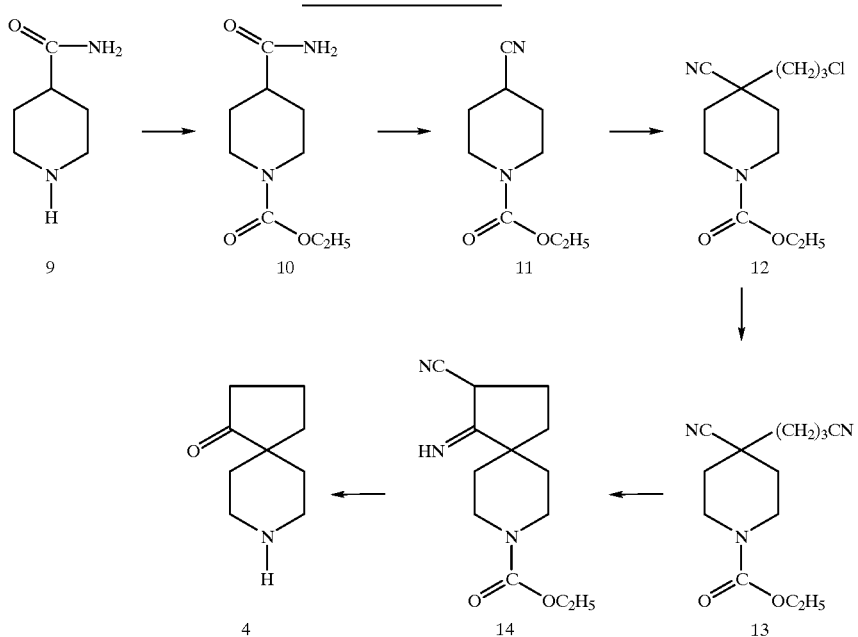

The spiro[cyclopent[b]indole-piperidines] and related compounds of the present invention are useful as agents for the relief of memory dysfunction, particularly dysfunctions associated with decreased cholinergic activity such as those found in Alzheimer's disease. Relief of memory dysfunction activity is demonstrated in the in vitro inhibition of acetylcholinesterase assay, an assay for the determination of the ability of a drug to inhibit the inactivation of acetylcholine, a neurotransmitter implicated in the etiology of memory dysfunction and Alzheimer's dementia. In this assay, a modification of a test described by G. L. Ellman, et al., Biochemical Pharmacology, 7, 88 (1961), the following reagents are prepared and employed:

1. 0.05 M Phosphate Buffer (pH 7.2)

A solution of monobasic sodium phosphate monohydrate (6.85 g) in distilled water (100 ml) is added to a solution of dibasic sodium phosphate heptahydrate (13.4 g) and distilled water (100 ml) until a pH of 7.2 was attained. The solution was diluted 1 to 10 with distilled water.

2. Substrate in Buffer

The 0.05 M Phosphate Buffer (pH 7.2) was added to acetylthiocholine (198 mg) to a total volume of 100 ml, i.e., a quantity sufficient (gs) to 100 ml.

3. 5,5-Dithiobisnitrobenzoic acid in Buffer

The 0.05 M Phosphate Buffer (pH 7.2) was added to 5.5-dithiobisnitrobenzoic acid to a total volume of 100 ml, i.e., a quantity sufficient (gs) to 100 ml.

4. Stock Solution of Drug

A 2 millimolar stock solution of the test drug is prepared in a quantity sufficient of either acetic acid or dimethyl sulfoxide to volume with 5,5-dithiobisnitrobenzoic acid in Buffer. Stock Solution of Drug is serially diluted (1:10) so that the final cuvette concentration is $10^{-4}$ molar.

Male Wistar rats are decapitated, brains rapidly removed, corpora striata dissected free, weighted and homogenized in 19 volumes (approximately 7 mg protein/ml) of 0.05 M Phosphate Buffer (pH 7.2) using a Potter-Elvejhem homogenizer. A 25 $\mu$l aliquot of this suspension is added to 1 ml of the vehicle or various concentrations of the test drug and preincubated for 10 minutes at 37° C. Enzyme activity is measured with a Beckman DU-50 spectrophotometer with the following software and instrument settings:

1. Kinetics Soft-Pac™ Module #598273;
2. Program #6 Kindata;
3. Source—Vis;
4. Wavelength—412 nm;
5. Sipper—none;
6. Cuvettes—2 ml cuvettes using auto 6-sampler;
7. Blank—1 for each substrate concentration;
8. Interval time—15 seconds (15 or 30 seconds for kinetics);
9. Total time—5 minutes (5 to 10 minutes for kinetics);
10. Plot—yes;
11. Span—autoscale;
12. Slope—increasing;
13. Results—yes (gives slope); and
14. Factor—1.

Reagents are added to the blank and sample cuvettes as follows:

1. Blank: 0.8 ml 5.5-Dithiobisnitrobenzoic Acid 0.8 ml Substrate in Buffer
2. Control: 0.8 ml 5.5-Dithiobisnitrobenzoic Acid/ Enzyme 0.8 ml Substrate in Buffer
3. Drug: 0.8 ml 5.5-Dithiobisnitrobenzoic Acid/Drug/ Enzyme 0.8 ml Substrate in Buffer Blank values are determined for each run to control for non-enzymatic hydrolysis of substrate and these values are automatically subtracted by the Kindata program available on kinetics soft-pac module. This program also calculates the rate of absorbance change for each cuvette.

For IC$_{50}$ Determinations

Substrate concentration is 10 millimolar diluted 1:2 in assay yielding final concentration of 5 millimolar. 5,5-dithiobisnitrobenzoic acid concentration is 0.5 millimolar yielding 0.25 millimolar final concentration.

$$\% \text{ Inhibition} = \frac{\text{Slope Control} - \text{Slope drug}}{\text{Slope Control}} \times 100$$

IC$_{50}$ values are calculated from log-probit analysis

TABLE I

| Compound | Inhibition of Acetylcholine-sterase Activity IC$_{50}(\mu M)$ |
|---|---|
| 1,4-dihydro-7-methoxy-4-methyl-1'-phenylmethylspiro [cyclopent[b]indole-3(2H),4'-piperidine] | 23.6 |
| 1,4-dihydro-7-hydroxy-4-methyl-1'-phenylmethylspiro [cyclopent[b]indole-3(2H),4'-piperidine] | 20.4 |
| 1,4-dihydro-4-methyl-7-methylaminocarbonyloxy-1'-phenylmethylspiro[cyclopent[b]indole-3(2H),4'-piperdine | 10.5 |
| 1,4-dihydro-7-dimethylaminocarbonyloxy-4-methylspiro [cyclopent[b]indole-3(2H),4'-piperidine | 64.0 |
| 1,4-dihydro-4-methylspiro[cyclopent[b]indole-3(2H), 4'-piperidine] | 84.1 |
| 1,4-dihydro-4-methyl-1'-(4-methoxyphenyl)methylspiro [cyclopent[b]indole-3(2H),4'-piperidine] | 65.2 |
| tacrine (reference) | 0.31 |

Relief of memory dysfunction is achieved when the present spiro[cyclopen[b]indole-piperidines] and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The spiro[cyclopent[b]indole-piperidines] of the present invention are also useful as agents for treating depression. Depression treatment is demonstrated in the in vitro inhibition of monoamine oxidase assay, an assay for the determination of the ability of a drug to inhibit the enzyme monoamine oxidase. In this assay, a modification of an assay described by M. V. Kindt, et al., Europ. J. Pharmacol. 146: 313–318 1988.

The following reagents are prepared:
1. Phosphate buffer (0.5 M), pH 7.4; 134.4 g dibasic sodium phosphate heptahydrate q.s. to 1 liter in distilled water (A) 17.3 g monobasic sodium phosphate q.s. to 250 ml in distilled water (B) Adjust pH of A to 7.4 by slowly adding B (volumes as needed) Dilute 1:10 in distilled water (0.05 M phosphate buffer, pH 7.4)
2. 0.25 M Sucrose (phosphate buffered): 21.4 g sucrose, q.s. to 250 ml with 0.05 M phosphate buffer
3. Substrate for monoamine oxidase-A:
   a. serotonin creatine sulphate (5-hydroxytryptamine) is obtained from Sigma Chemical Company. A 5 mM stock solution is made up in 0.01 N-hydrochloric acid. The solution is used to dilute the specific activity of the [$^3$H]-hydroxytryptamine.

b. [$^3$H]-5-hydroxytryptamine binoxalate (20–30 Ci/mmol) is obtained from New England Nuclear.

v. Add 12 pi of [$^3$H]-5-hydroxytryptamine to 2 ml of the 5 mM 5-hydroxytryptamine solution. (Final amine concentration in the assay is 200 $\mu$M: see below.)

4. Substrate for monoamine oxidase-B
 a. β-phenethylamine is obtained from Sigma Chemical Company. A 5 mM stock solution is made up in 0.01 N-hydrochloric acid. The solution is used to dilute the specific activity of the [$^{14}$C]-β-phenethylamine. phenethylamine.
 b. β-[ethyl- 1-$^{14}$C]-phenethylamine hydrochloride (40–50 mCi/mmol) is obtained from New England Nuclear.
 c. Add 12 $\mu$l of [$^{14}$C]-β-phenethylamine to 2 ml of the 5 mM β-phenethylamine solution. (Final amine concentration in the assay is 200 $\mu$M: see below.)

5. Equal amounts of monoamine oxidase-A (5-hydroxytryptamine) and monoamine oxidase-B (P-phenethylamine) substrates are combined for simultaneously testing both monoamine oxidase types, i.e., mixed stock solution of 2.5 mM 5-hydroxytryptamine and 2.5 mM β-phenethylamine. 40 $\mu$l of this mixed solution gives a 200 $\mu$M final concentration of each amine in the assay. When testing only one monoamine oxidase type, the individual 5 mM stock solutions must be diluted 1:1 with distilled water prior to adding 40 $\mu$l to the incubation mixture; i.e., same 200 $\mu$M final amine concentration. 6. Stock solutions of test drugs are made up in appropriate vehicles and serially diluted to give final concentrations ranging from $10^{-7}$ to $10^{-3}$ molar in the assay. Lower concentrations can be made for more potent drugs.

Tissue Preparation

Male Wistar rats weighing 150–250 grams were sacrificed and the brains rapidly removed. Whole brain minus cerebellum was homogenized in 30 volumes of ice-cold, phosphate-buffered 0.25 M sucrose, using a Potter-Elvejhem homogenizer. The homogenate was centrifuged at 1000 g for 10 minutes and the supernatant ($S_1$) decanted and recentrifuged at 18,000 g for 20 minutes. The resulting pellet ($P_2$) was resuspended in fresh 0.25 M sucrose and serves as the tissue source for mitochondrial monoamine oxidase.

C. Assay

10 $\mu$l 0.5 M phosphate buffer, pH 7.4

50 $\mu$l water or appropriate drug concentration

400 $\mu$l tissue suspension

Tubes are preincubated for 15 minutes at 37° C. and the assay is started by adding 40 $\mu$l of combined substrate ([$^3$H]-5-hydroxytryptamine and [$^4$C]-β-phenethylamine) at 15 second intervals. The tubes are incubated for 30 minutes at 37° C. and the reaction stopped by the addition of 0.3 ml 2N- hydrochloric acid. Tissue blank values are determined by adding the acid before the radioactive substrate. The oxidative products of the reaction are extracted with ethylacetate/toluene (1:1). Add 5 ml of this mixture to the tubes, vortex for 15 seconds to extract the deaminated metabolites into the organic phase and allow to separate from the aqueous phase. Place tubes in acetone/dry ice bath to freeze the aqueous layer. When this layer is frozen, pour off the top organic layer into a scintillation vial. Add 10 ml Liquiscint and count the samples using window settings for $^{14}$C in one channel and $^3$H in the second channel. $IC_{50}$ values are determined by log-probit analysis.

Results

TABLE 11

| Compound | Monoamine Oxidase A $IC_{50}(\mu M)$ | Monoamine Oxidase B |
|---|---|---|
| 8-azaspiro[4,5]decane-1-[N'-(4-methoxy)phenyl]hydrazone | 37.2 | 3.7 |
| 1,4-dihydro-1'-(3-methoxyphenyl)methyl-4-methylspiro[cyclopent[b]indole-3(2H),4'-piperidine | 51.2 | — |
| 1,4-dihydro-1'-(4-methoxyphenyl)methyl-4-methylspiro[cyclopent[b]indole-3-(2H),4'piperidine] | 98.6 | 124.6 |
| brofaromine (reference) | 0.18 | 23.4 |

Depression treatment is achieved when the present spiro[cyclopent[b]indole-piperidiens] and related compounds are administered to a subject requiring such treatment as an effective oral, parenteral or intravenous dose of from 0.10 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Acetylcholinesterase inhibitors and monoamine oxidase inhibitors are known in the art as being useful as relievers of memory dysfunction and as antidepressants, respectively. (See V. Kumar in Alzheimer's Disease: Therapeutic Strategies, E. Giacobini and R. Becker Eds.; Birkhauser, Boston 1994 for memory dysfunction utility and K. F. Tipton in Biochemical and Pharmacological Aspects of Depression, K. F. Tipton and U. B. H. Youdin, Eds., Taylor and Francis, London 1989 for antidepressant utility.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compounds, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl, salicylate, or orange flavoring may be added. When the dosage unit is a capsule it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple vials made of glass or plastic.

The following examples are for illustrative purposes only and are not to be construed as limiting the invention in any way whatsoever.

EXAMPLE 1

1,4-Dihydrospiro[cyclopentrblindole-3(2H), 4'-piperidine] hydrochloride hemihydrate A solution of 8-azaspiro[4,5]decane-1-(N'-phenyl) hydrazone hydrochloride (1.0 g) in ethanolic hydrochloric acid (15 ml) was heated on a steam bath for 90 min, with stirring, and then concentrated in vacuo. The residue was flash chromatographed (silica gel), eluting with 15% methanol/dichloromethane. The appropriate fractions were collected and concentrated. The residue was recrystallized from ethanol/ethyl acetate to give 0.4 g (43%) of product, mp 315–316° C.

Analysis:
Calculated for $C_{15}H_{18}N_2 \cdot HCl \cdot \frac{1}{2}H_2O$: 66.29%C 7.42%H 10.31%N
Found: 66.16%C 7.19%H 10.18%N

EXAMPLE 2

1'-Benzoyl-1,4-dihydrospiro[cyclopentrblindole-3(2H), 4'-piperidine]

To a solution of 1,4-dihydrospiro[cyclopent[b]indole-3(2H), 4'-piperidine] hydrochloride (1.0 g) and potassium carbonate (0.8 g) in acetonitrile (10 ml) was added benzoyl chloride (0.5 g), under nitrogen, with stirring. The reaction mixture was heated under reflux for 5 hrs and allowed to cool to ambient temperature. Ethyl acetate (200 ml) was added, and the mixture was washed with water and saturated sodium hydroxide solution, dried over anhydrous magnesium sulfate, filtered and the filtrate was concentrated in vacuo. The residue was flash chromatographed (silica gel), eluting with 0.5% methanol/dichloromethane. The appropriate fractions were collected and concentrated to give 0.40 g (33%) of product, mp 231–232° C.

Analysis:
Calculated for $C_{22}H_{22}N_2$: 79.97%C 6.71%H 8.48%N
Found: 79.67%C 6.74%H 8.43%N

EXAMPLE 3

1,4-Dihydro-7-methoxyspiro[cyclopentfblindole-3(2H), 4'-piperdine]hydrochloride

A solution of 8-azaspiro[4,5]decane-1-[N'-(4-methoxy)phenyl]hydrazone hydrochloride (2.0 g) in ethanolic hydrochloric acid (10 ml) and water (0.5 ml) was heated on a steam bath for 1 hr, with stirring, and then concentrated in vacuo. The residue was flash chromatographed (silica gel), eluting with 5% methanol/dichloromethane. The appropriate fractions were collected and concentrated. The residue was recrystallized from ethanol to give 0.5 g (26%) of product mp>280° C.

Analysis:
Calculated for $C_{16}H_{20}N_2O$ *HCl: 65.63%C 7.23%H 9.57%N
Found: 65.52%C 7.49%H 9.54%N

EXAMPLE 4

1-[4-[3-(7-Fluoro-1,4-dihydrospirorcyclopent[b]indole-3(2H)4'-piperidinel-1'-yl) propoxy]-3-methoxyphenyl]ethanone hydrate To a solution of 1,4-dihydro-7-fluorospiro[cyclopent[b]indole-3(2H), 4'-piperidine] (3.00 g) in acetonitrile (30 ml) was added cesium carbonate (6.97 g) and 1-[4-(3-bromopropoxy)-3-methoxyphenyl]ethanone (3.38 g), under nitrogen, with stirring. The reaction mixture was heated at 80° C. for 3 hrs and allowed to cool to ambient temperature. The mixture was extracted with ethyl acetate. The extracts were washed with water, dried over anhydrous magnesium sulfate, filtered, and the filtrate was concentrated in vacuo. The residue was flashed chromatographed (silica gel) eluting with 1% acetone/dichloromethane. The appropriate fractions were collected and concentrated to give 1.00 g (30%) of product, mp 165–166° C.

Analysis:
Calculated for $C_{27}H_{31}FN_2O_3 \cdot H_2O$: 69.21%C 7.10%H 5.98%N
Found: 69.00%C 6.85%H 5.82%N

EXAMPLE 5

1,4-Dihydro-4-methylspirofcyclopentrblindole-3(2H), 4'-piperidinel hydrochloride A solution of 8-azaspiro[4,5]decane-1-one hydrochloride (5.2 g) in 95% ethanolic hydrochloric acid (30 ml) and 1-methyl-1-phenylhydrazine (5 g) was heated overnight on a steam bath, under nitrogen. The reaction mixture was cooled to ambient temperature, methanol was added and the mixture was concentrated in vacuo. The residue was flash chromatographed (silica gel) eluting with 10% methanol/ dichloromethane. The appropriate fractions were collected and concentrated to afford 7.4 g (95%) of product, mp >270° C.
Analysis:
Calculated for $C_{16}H_{20}N_2 \cdot HCl$: 69.43%C 7.65%H 10.12%N
Found: 68.90%C 7.55%H 9.94%N

EXAMPLE 6

1,4-Dihydro-1'-(3-methoxyphenyl)methyl-4-methylspiro[cyclopent[b]indole-3(2H), 4'piperidine]

A solution of 1,4-dihydro-4-methylspiro[cyclopent[b]indole-3(2H), 4'-piperidine] (2.5 g) and triethylamine (2.9 ml) in dichloromethane (100 ml) and 3-(chloromethyl) anisole (1.95 g) was stirred overnight at ambient temperature, under nitrogen. Saturated sodium chloride solution was added and the mixture was extracted with dichloromethane. The extracts were dried over anhydrous magnesium sulfate, filtered, and the filtrate was concentrated in vacuo. The residue was flashed chromatographed (silica gel), eluting with 10% anhydrous acetone/dichloromethane. The appropriate fractions were collected and concentrated to give 1.3 g (35%) of product, mp 100–101° C.
Analysis:
Calculated for $C_{24}H_{28}N_2O$: 79.96%C 7.83%H 7.77%N
Found: 79.63%C 7.80%H 7.67%N

EXAMPLE 7

1,4-Dihydro-7-methoxy-4-methylspiro[cyclopent[b]indole-3(2H),4'-piperidine]hydrochloride A solution of 8-azaspiro[4,5]decane-1-[N'-(4-methoxy)phenyl-N'-methyl]hydrazone hydrochloride (2.5 g) in ethanolic hydrochloric acid (20 ml) and water (0.5 ml) was heated on a steam bath for 1 hr, with stirring, and then concentrated in vacuo. The residue was flash chromatographed (silica gel), eluting with 10% methanol/ dichloromethane. The appropriate fractions were collected and concentrated. The residue was recrystallized from ethanol to give 1.1 g (46%) of product, mp 278–279° C.
Analysis:
Calculated for $C_{17}H_{22}N_2O \cdot HCl$: 66.55%C 7.56%H 9.13%N
Found: 66.45%C 7.86%H 9.14%N

EXAMPLE 8

1'-Benzoyl-1,4-dihydro-7-methoxy-4-methylspiro [cyclopent[b]indole-3(2H), 4'-piperidine]hydrate To a solution of 1,4-dihydro-7-methoxy-4-methylspiro [cyclopent[b]indole-3(2H), 4'-piperidine] hydrochloride (0.50 g) and triethylamine (0.33 g) in dichloromethane (50 ml) was added benzoyl chloride (0.23 g) at 0° C., under nitrogen, with stirring. The reaction mixture was stirred for 5 hrs at ambient temperature. Dichloromethane (200 ml) was added and the mixture was washed with water and saturated sodium chloride solution. The organic layer was dried over anhydrous magnesium sulfate, filtered, and the filtrate was concentrated in vacuo. The residue was flash chromatographed (silica gel), eluting with 5% ethyl acetate/ dichloromethane. The appropriate fractions were collected and concentrated to give 0.40 g (66%) of product, mp 197–198° C.

Analysis:
Calculated for $C_{24}H_2N_2O_2 \cdot H_2O$: 73.44%C 7.19%H 7.14%N
Found: 73.90%C 6.76%H 6.95%N

EXAMPLE 9

1,4-Dihydro-7-methoxy-4-methyl-4'phenylmethylspiro[cyclopent-b1indole-3(2H), 4'-piperidine]hydrochloride To a solution of 1,4-dihydro-7-methoxy-4-methylspiro [cyclopent[b]indole-3(2H), 4'-piperidine hydrochloride (0.50 g) and triethylamine (0.33 g) in dichloromethane (50 ml) was added benzyl bromide (0.28 g) at 0° C., under nitrogen, with stirring. The reaction mixture was stirred for 72 hrs at ambient temperature. Dichloromethane (200 ml) was added and the mixture was washed with water and saturated sodium chloride solution. The organic layer was dried over anhydrous sodium sulfate, filtered, and the filtrate was concentrated in vacuo. The residue was flash chromatographed (silica gel), eluting with 25% ethyl acetate/ dichloromethane. The appropriate fractions were collected and concentrated. The residue was dissolved into ethyl acetate and treated with ethereal hydrogen chloride. The precipitate was recrystallized from ethanol/ethyl acetate to give 0.40 g (68%) of product, mp 253–254° C.
Analysis:
Calculated for $C_{24}H_{28}N_2O*HCl$: 72.62%C 7.36%H 7.06%N
Found: 72.23%C 7.51%H 6.99%N

EXAMPLE 10

1,4-Dihydro-7-hydroxy-4-methy-1'-phenylmethylspiro[cyclopent[b]indole-3(2H), 4'-piperidine hydrochloride A solution of 1,4-dihydro-7-methoxy-4-methyl-1'-phenylmethylspiro[cyclopent[b]indole-3(2H), 4'-piperidine (1.7 g) and 48% hydrobromic acid (10 ml) was heated to 95° C, under nitrogen, with stirring. The reaction mixture was stirred for 3 hrs. Dichloromethane (150 ml) was added, and the mixture was washed with saturated sodium bicarbonate solution and saturated sodium chloride solution. The layers were separated and the organic layer was dried over anhydrous sodium sulfate, filtered, and the filtrate was concentrated in vacuo. The residue was flash chromatographed (silica gel), eluting with 25% ethyl acetate/ dichloromethane. The appropriate fractions were collected and concentrated. This free base was converted to the hydrochloride salt to give 1.3 g (80%) of product, mp 189–190° C.
Analysis:
Calculated for $C_{23}H_{26}N_2O \cdot HCl$: 72.14%C 7.1 1%H 7.32%N
Found: 71.72%C 7.34%H 7.21%N

EXAMPLE 11

1,4-Dihydro-4-methyl-7-methylaminocarbonyloxy-1'-phenylmethoylspiro [cyclopent[b]indole-3(2H), 4'-piperidine]

To a solution of 1,4-dihydro-7-hydroxy4-methyl-1+-phenylmethylspiro[cyclopent[b]indole-3(2H), 4'-piperidinel (0.25 g) and copper (I) chloride (0.01 g) in dichloromethane (10 ml) was added methyl isocyanate (0.04 g), under nitrogen, with stirring. The reaction mixture was stirred for 24 hrs. The mixture was flash chromatographed (neutral alumina) and eluted with 25% ethyl acetate/ dichloromethane. The appropriate fractions were collected and concentrated to give 0.2 g (69%) of product, mp 189–190° C.
Analysis:
Calculated for $C_{25}H_{29}N_3O_2$: 74.41%C 7.24%H 10.41%N
Found: 74.04%C 7.05%H 10.16%N

EXAMPLE 12

1,4-Dihydro-7-dimethylaminocarbonyloxy-4-methylspirorcyclopent[b]indole-3(2H), 4'-piperidine]hemihydrate To a solution of 1,4-dihydro-7-hydroxy-4-methylspiro [cyclopent[b]indole-3(2H), 4-piperidine] (0.61 g) and cesium carbonate (1.55 g) in acetonitrile (100 ml) was added dimethylcarbamyl chloride (0.25 g), under nitrogen, with stirring. The reaction mixture was stirred for 24 hrs, diluted with ethyl acetate, and the mixture was washed with saturated sodium chloride solution. The layers were separated, and the organic layer was dried over anhydrous sodium sulfate, filtered, and the filtrate was concentrated in vacuo. The residue was flash chromatographed (silica), eluting with 5% methanolldichloromethane. The appropriate fractions were collected and concentrated. The residue was recrystallized from ethyl acetate/petroleum ether. The precipitate was flash chromatographed (silica), eluting with 25% ethyl acetateldichloromethane to give 0.1 g (15%) of product, mp 110–111° C.
Analysis:
Calculated for $C_{19}H_{25}N_3O_2 \cdot \frac{1}{2}H_2O$: 68.83%C 7.79%H 12.49%N
Found: 68.73%C 7.97%H 12.44%N

EXAMPLE 13

1,4-Dihydro-4'-(4-methoxyphenyl)methyl-4-methylspirorcyclopent[b]indole-3(2H), 4'-piperidine]

A solution of 1,4-dihydro-4-methylspiro[cyclopent[b] indole-3(2H), 4'-piperidine] (2.5 g) and triethylamine (2.9 ml) in dichloromethane (100 ml) and 4-(chloromethyl) anisole (1.95 g) was allowed to stand overnight at ambient temperature, under nitrogen, with stirring. Saturated sodium chloride solution was added and the mixture was extracted with dichloromethane. The layers were separated, and the organic phase was dried over anhydrous magnesium sulfate and filtered. The filtrate was concentrated in vacuo. The residue was flash chromatographed (silica gel), eluting with 7.5% acetone/dichloromethane. The appropriate fractions were collected and concentrated to give 1.5 g (40%) of product, mp 39–40° C.
Analysis:
Calculated for $C_{24}H_{28}N_2O$: 79.96%C 7.83%H 7.77%N
Found: 79.65%C 7.92%H 7.64%N

EXAMPLE 14

Ethyl 4-(3-chloropropyl)-4-cyano-1-piperidinecarboxylate

To a solution of ethyl 4-cyano-1-piperidinecarboxylate (6.0 g) in tetrahydrofuran (120 ml) at –70° C., under nitrogen, was added a solution of lithium diisopropylamide (4.6 g) in tetrahydrofuran (21.5 ml), dropwise, with stirring. The reaction was allowed to warm to –10° C. and after 30 min was recooled to –70° C. A solution of 1-chloro-3-iodopropane (7.4 g) in tetrahydrofuran (20 ml) was added to the mixture over 30 min. The reaction mixture was quenched with water and allowed to warm to ambient temperature. The mixture was extracted with ethyl acetate. The extracts were washed with water, saturated sodium chloride solution, dried over anhydrous magnesium sulfate and filtered. The filtrate was concentrated in vacuo and the residue was flash chromatographed (silica), eluting with 2:1 heptane/ethyl acetate. The appropriate fractions were collected and concentrated to afford 5.5 g ( 64%) of product.
Analysis:
Calculated for $C_{12}Hl_9ClN_2O_2$: 55.70%C 7.40%H 10.83%N
Found: 55.88%C 7.67%H 10.80%N

EXAMPLE 15

Ethyl 4-(3-cyanopropyl)-4-cyano-1-piperidinecarboxylate

To a solution of ethyl 4-(3-chloropropyl)4-cyano-1-piperidinecarboxylate (12.7 g) in dimethylformamide (250 ml) was added sodium cyanide (24 g) under nitrogen, with stirring. The mixture was warmed at 140° C. overnight and then cooled to ambient temperature, diluted with water and extracted with ethyl acetate. The organic extracts were washed with saturated sodium chloride solution and water, dried over anhydrous magnesium sulfate and filtered. The filtrate was concentrated in vacuo. The residue was chromatographed, eluting with 2:1 heptane/ethyl acetate. The appropriate fractions were collected and concentrated to give 10.8 g (88.5%) of product. A portion was distilled to give the analytical sample, bp196–201° C. (4 mm of mercury).
Analysis:
Calculated for $C_{13}Hl_9N_3O_2$: 62.63%C 7.68%H 16.85%N
Found: 62.27%C 7.85%H 16.63%N

EXAMPLE 16

8-Azaspiro[4,5]decane-1-[N'-(4-bromo)phenyl] hydrazone hydrochloride

To a solution of 8-azaspiro[4,5]decane-1-one hydrochloride (2.5 g) in 95% ethanol (10 ml) was added acetic acid (0.5 ml) and 4-bromophenylhydrazine (2.5 g), under nitrogen, with stirring. The mixture was heated on a steam bath for 20 min, cooled to 0° C. and filtered. The filter cake was washed with 1M hydrochloric acid solution and chilled ethanol (10 ml) and dried in vacuo to give 4.2 g (89%) of product, mp 285–286° C.
Analysis:
Calculated for $C_{15}H_{21}BrClN_3$: 50.23%C 5.90%H 11.71%N
Found: 50.36%C 6.04%H 11.45%N

EXAMPLE 17

8-Azaspiror4,51decane-1-[N'-(4-methoxy) phenyllhydrazone hydrochloride

To a solution of 8-azaspiro[4,5]decane-1-one hydrochloride (2.5 g) in 95% ethanol (10 ml) was added acetic acid (0.5 ml) and 4-methoxyphenylhydrazine (1.8 g), under nitrogen, with stirring. The mixture was heated on a steam bath for 15 min, cooled to 0C and filtered. The filter cake was washed with 1 M hydrochloric acid solution and chilled ethanol (10 ml) and dried in vacuo to give 2.6 g (73%) of product, mp 252–253° C.
Analysis:
Calculated for $C_{16}H_{24}ClN_3O$: 62.02%C 7.81%H 13.56%N
Found: 62.15%C 8.09%H 13.61%N

EXAMPLE 18

8-Azaspiror4,51decane-1-[N'-(4-methoxy)phenyl-N'-methyl]hydrazone hydrochloride To a solution of 8-azaspiro[4,5]decane-1-one hydrochloride (5.2 g) in 95% ethanol (30 ml) was added acetic acid (1 ml) and 1-(4-methoxy)phenyl-1-methylhydrazine (5.0 g), under nitrogen, with stirring. The mixture was heated on a steam bath for 2 hrs and was concentrated in vacuo. The residue was recrystallized from ethyl acetate. The precipitate was titurated with ethanol/ethyl acetate and then dichloromethane/petroleum ether to give 3.6 g (36%) of product, mp 177–178° C.
Analysis:
Calculated for $C_{17}H_{26}ClN_3O$: 63.05%C 8.09%H 12.97%N
Found: 62.65%C 8.24%H 12.76%N

EXAMPLE 19

8-Azaspirof4,5]decane-1-(N'-phenyl)hydrazone hydrochloride

To a solution of 8-azaspiro[4,5]decane-1-one hydrochloride (5.0 g) in ethanol (15 ml) was added acetic acid (1 ml) and phenylhydrazine (2.85 g), under nitrogen, with stirring. The mixture was heated on a steam bath for 15 min, cooled to 0° C. and filtered. The filter cake was washed with IM hydrochloric acid solution and chilled ethanol (10 ml) and dried in vacuo to give 5.5 g (85%) of product, mp 261–262° C.
Analysis:
Calculated for $C_{15}H_{22}ClN_3$: 64.39%C 7.92%H 15.02%N
Found: 64.34%C 7.92%H 15.13%N

EXAMPLE 20

Ethyl 2-cyano-1-imino-8-azaspiror4,5]decane-8-carboxylate hemihydrate

To a solution of ethyl 4-(3-cyanopropyl)-4-cyano-1-piperidinecarboxylate (5 g) in tetrahydrofuran (75 ml) was added lithium diisopropylamide (2.5 g) at −70° C., under nitrogen, with stirring. The reaction mixture was warmed to ambient temperature over 10 min and heated at reflux for 90 min. The reaction mixture was cooled to ambient temperature, neutralized with 5% hydrochloric acid and extracted with ethyl acetate. The organic layer was dried over anhydrous magnesium sulfate, filtered, and the filtrate was concentrated in vacuo. The residue was recrystallized from chloroformn/petroleum ether to afford 1.8 g (36%) of product, mp 215–216° C.
Analysis:
Calculated for $C_{13}H_{20}N_3O_3$: 60.45%C 7.80%H 16.27%N
Found: 60.62%N 7.51%H 16.01%N

EXAMPLE 21

8-Azaspiro[4,5]decane-1-one hydrochloride

A solution of 4-cyano-1-irnino-8-azaspiro [4,5]decane (2.6 g) in 6N hydrochloric acid (100 ml) was heated at 95° C. overnight. The reaction mixture was concentrated in vacuo. The residue was flash chromatographed (silica gel), eluting with 20% methanol/dichloromethane. The appropriate fractions were collected and concentrated. The residue was recrystallized from ethanol to give 0.8 g (55%) of product, mp 212–213° C.
Analysis:
Calculated for $C_9H_{16}ClNO$: 56.99%C 8.50%H 7.38%N
Found: 56.87%C 8.34%H 7.31%N

EXAMPLE 22

4-Acetamido-N-ethox yearbonylpiperdine

A solution of 4-acetamidopiperidine (20.7 g), sodium bicarbonate (10.6 g) and water (300 ml) was cooled to 0° C., and 17.7 g of ethyl chloroformate was added dropwise, with stirring. Upon completion of the addition, the reaction mixture was allowed to warm to ambient temperature and was diluted with water and ethyl acetate. The layers were separated, and the organic layer was washed with saturated sodium chloride solution, dried over anhydrous magnesium sulfate and filtered. The filtrate was evaporated to give 32.2 g (100%) of product.

EXAMPLE 23

4-Cyano-N-ethoxycarbonylpiperidine

A mixture of 4-acetamido-N-ethoxycarbonylpiperidine (17.0 g) and acetonitrile (200 ml) was cooled to 0° C., and 15.5 g of thionyl chloride was added dropwise, under nitrogen, with stirring. The reaction mixture was allowed to warm to ambient temperature. To the reaction mixture was added 2-propanol (20 ml) and the mixture was heated under reflux for 1 hr. Ethyl acetate was added, the layers were separated, and the organic phase was washed with 5% sodium bicarbonate solution, dried over anhydrous magnesium sulfate, filtered, and the filtrate was concentrated. The residue was chromatographed on a preparatory liquid chromatograph, eluting with 4:1-heptane:ethyl acetate. The appropriate fractions were collected and evaporated to give 15 g of residue. A 4-g sample of the residue was distilled to give 3.5 g (84.6%) of product, bp 130° C. (4 mm mercury).

We claim:
1. A compound of the formula

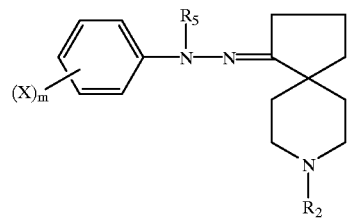

wherein $R_2$ is hydrogen or loweralkyl; $R_5$ is hydrogen or loweralkyl; and X is hydrogen, halogen, loweralkoxy, loweralkyl, hydroxy or trifluoromethyl and m is 1 or 2; the optical isomers thereof; or the pharmaceutically acceptable salt thereof.

2. A compound according to claim 1 which is 8-azaspiro[4,5]decane-1-(N'-phenyl) hydrazone.

3. The compound according to claim 7 which is 8-azaspiro[4,5]decane-1-[N'-(4-methoxy) phenyl-N'-methyl]hydrazone.

4. The compound according to claim 7 which is 8-azaspiro[4,5]decane-1-[N'-(4-methoxy) phenyl] hydrazone.

5. The compound according to claim 7 which is 8-azaspiro[4,5]decane-1-[N+-(4-bromo) phenyl]hydrazone.

* * * * *